US00PP20892P2

(12) United States Plant Patent
Bradford

(10) Patent No.: US PP20,892 P2
(45) Date of Patent: Mar. 30, 2010

(54) INTERSPECIFIC TREE NAMED 'BLACKRED XII'

(50) Latin Name: ***Prunus* sp.**
Varietal Denomination: Blackred XII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,593

(22) Filed: Dec. 15, 2008

(51) Int. Cl.
*A01H 5/00* (2006.01)

(52) U.S. Cl. ..... Plt./180

(58) Field of Classification Search ..... Plt./180, Plt./184, 186
See application file for complete search history.

(56) References Cited

U.S. PATENT DOCUMENTS

PP14,220 P2 10/2003 Bradford
PP16,369 P2 3/2006 Bradford

*Primary Examiner*—June Hwu

(57) ABSTRACT

The present invention relates to an interspecific tree and more particularly to a new and distinct variety broadly characterized by a medium to large size, moderately vigorous, hardy, and medium productive tree. Being self-unfruitful, the present variety requires cross pollination from an apricot, interspecific, or plum that blooms during the mid to late season. The present variety's abundance of blossoms and pollen entices strong bee activity to facilitate pollination. The fruit matures under the ecological conditions described during late September, with first picking on Sep. 27, 2008. The fruit is medium to large in size, mostly black in skin color, clingstone in type, nearly globose in shape, and mostly red to orange in flesh color.

1 Drawing Sheet

Botanical classification: *Prunus* sp.
Varietal denomination: 'BLACKRED XII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred XII'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2003 one such house containing an unpatented purple plum, code named '42P1156', was crossed by me in this manner. To pollinate this purple plum, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2006 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, '42P1156', by being self-unfruitful and by producing fruit that is purple to black in skin color, firm in texture, and globose in shape, but is distinguished therefrom by producing fruit that is pink to red in flesh color instead of yellow, that is much sweeter in flavor, and that matures about forty days later.

The present variety is similar to 'September Yummy' plum (U.S. Plant Pat. No. 14,220) by being self-unfruitful and by producing fruit that ripens in the late season, that is firm in texture, and that is very good in flavor, but is distinguished therefrom by producing fruit that is mostly black in skin color instead of red, that is more heavily red in flesh color, that is clingstone instead of semi-freestone, and that matures about ten days earlier. It is to be noted that the patent for 'September Yummy' plum describes a first pick date of Sep. 10, 2002. Since the filing of that patent, it has been established that the average commercial first pick date is closer to October 10th.

The present variety is similar to 'Plumsweet V' interspecific tree (U.S. Plant Pat. No. 16,369) by being self-unfruitful and by producing fruit that is clingstone in type, that is mostly globose in shape, that matures in the late season, and that is very good in flavor, but is distinguished therefrom by producing fruit that is mostly black in skin color instead of mostly purple, that has more red and orange in its flesh color, that is larger in size, and that matures about thirty days later.

SUMMARY OF VARIETY

The present interspecific variety is characterized by a medium to large size, moderately vigorous, hardy, and medium productive tree. Being self-unfruitful, the present variety requires cross pollination from an apricot, interspecific, or plum that blooms during the mid to late season. The present variety's abundance of blossoms and pollen entices strong bee activity to facilitate pollination. The fruit matures under the ecological conditions described during late September, with first picking on Sep. 27, 2008. The fruit is medium to large in size, mostly black in skin color, clingstone in type, nearly globose in shape, and mostly red to orange in flesh color.

DRAWING

The accompanying photograph consists of four whole fruits positioned to display the characteristics of the skin color and form, two half fruits divided to reveal the flesh and stone, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of shipping ripe on Sep. 30, 2008, on the original tree during its fifth growing season. The flower and bud descriptions were developed during the previous blooming season. All major color code designations are by reference to the Inter-Society Color Council, National Bureau of Standards. Common color names are also used occasionally.

Parentage

Seed parent: 42P1156 plum (unpatented).
Pollen parent: Unknown.

Tree

Size: Medium to large, reaching a height of 13' [3.96 m.] and a spread of 7' [2.13 m.] after five growing seasons utilizing typical pruning.

Vigor: Medium vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium production, thinning usually necessary.

Fertility: Self-unfruitful, requiring cross pollination by a suitable mid to late seasonal blooming apricot, interspecific, or plum, such as 'Redyummy' plum (U.S. Plant Pat. No. 18,663).

Bearing: Regular bearer, with no crop failures observed.

Trunk:

- *Size.*—Medium, reaching a maximum diameter of 4⅛" [104.8 mm.] after the fifth growing season.
- *Texture.*—Medium shaggy.
- *Bark Color.*—A Grayish brown [61. gy.Br] and Dark yellowish brown [78. d.yBr] variegation with Light yellowish brown [76. l.yBr] crevices present.
- *Lenticels.*—Approximate Number Per Square Inch: 20. Color: Moderate orange [53. m.O]. Average Size: ¼" [6.4 mm.]. Shape: Elongated, eye-shaped.

Branches:

- *Size.*—Diameter of limb is 2¼" [57.2 mm.] measured 12" above first limb, 1¼" [31.8 mm.] measured 12" above first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: Grayish brown [61. gy.Br].
- *Lenticels.*—Number Per Square Inch: More than 60 on second year wood. Color: Dark orange yellow [72. d.OY]. Average Size: 1/32" [0.8 mm.]. Shape: Eye-shaped.

Leaves:

- *Size.*—Medium. Average Length: 4½" [114.3 mm.]. Average Width: 1⅞" [47.6 mm.].
- *Arrangement.*—Alternate.
- *Thickness.*—Medium.
- *Form.*—Elliptical.
- *Apex.*—Acuminate.
- *Base.*—Acute with an average angle base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ½" [12.7 mm.]. Average Thickness: 1/16" [1.6 mm.]. Color: Light yellow green [119. l.YG] with some Light grayish red [18. l.gy.R] on topside.
- *Stipules.*—Number: Usually2 per leaf, up to 6 per growing tip. Average Length: ⅜" [9.5 mm.]. Color: Light yellow green [119. l.YG] becoming Deep reddish Brown [41. deep rBr] with age.
- *Glands.*—Number: Mostly 2 to 4 per leaf. Position: Both alternately and oppositely positioned at the intersection of the petiole and the leaf blade. Size: Medium. Form: Globose. Color: Brilliant yellow green [116. brill.YG] with a Dark reddish brown [44. d.rBr] center. Leaf buds: Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip Color.*—White [263. White].

Flowers: Perfect, complete, perigynous, usually a single pistil, about thirty stamens, five sepals and petal locations alternately positioned.

- *Average flower diameter.*—1 1/16" [27.0 mm.].
- *Number of petals.*—Five, no double blossoms observed.
- *Petal shape.*—Oval to circular.

*Petal margin.*—Entire, smooth to slightly wavy.
*Average petal diameter.*—½" [12.7 mm.].
*Average petal length.*—⅝" [15.9 mm.].
*Petal apex.*—Rounded.
*Petal base.*—Obtuse.
*Petal color.*—White [263. White] on both sides.
*Anther color.*—Moderate orange yellow [71. m.OY].
*Stigma color.*—Brilliant greenish yellow [98. brill.gY].
*Sepal color.*—Brilliant yellow green [116. brill.YG] on the outer surface with Grayish red [19. gy.R] areas toward the edges.
*Sepal length.*—5/32" [4.0 mm.].
*Sepal width.*—⅛" [3.2 mm.].
*Sepal apex.*—Rounded to elliptical to match the width and length.
*Sepal margin.*—Fairly smooth, with slight serration toward the apex.
*Average pistil length.*—⅝" [15.9 mm.].
*Average stamen length.*—½" [12.7 mm.].
*Fragrance.*—Moderate.
*Pollen production.*—Strong, bee enticing.
*Blooming period.*—Late, four days after 'Santa Rosa' plum (unpatented).
*Onset of bloom.*—One percent on Mar. 3, 2008.
*Date of full bloom.*—Mar. 11, 2008.
*Duration of bloom.*—One to two weeks, dependent on ambient temperature.
*Bloom density.*—Heavy.
*Number per cluster.*—2 to 10, average 5.

FRUIT

Maturity when described: Shipping ripe, Sep. 30, 2008.
Date of first picking: Sep. 27, 2008.
Date of last picking: Oct. 10, 2008.
Size: Uniform, medium to large.
*Average diameter axially.*—2½" [63.5 mm.].
*Average diameter across cheek plane.*—2⅝" [66.7 mm.].
*Average diameter across suture plane.*—2⅝" [66.7 mm.].
*Typical weight.*—5.2 ounces [147.4 grams].
Form: Uniform, globose, symmetrical.
*Longitudinal section form.*—Round.
*Transverse section through diameter.*—Round.
Suture: An inconspicuous shallow groove extending from the base just to the pistil point.
Ventral surface: Rounded, very slightly lipped on both sides.
Lips: Slightly unequal.
Cavity: Flaring, rounded to slightly elongated in suture plane, suture showing on one side.
*Depth.*—7/16" [11.1 mm.].
*Breadth.*—15/16" [23.8 mm.].
Base: Truncate, somewhat cordate if viewed parallel to the suture.
Apex: Rounded with a slight hump near the pistil point.
Pistil point: An inconspicuous dot located at the end of the suture.
Stem: Medium.
*Average length.*—9/16" [14.3 mm.].
*Average width.*—3/32" [2.4 mm.].
Skin:
*Thickness.*—Medium.
*Surface.*—Smooth.
*Tenacity.*—Tenacious to the flesh.
*Astringency.*—Slight.
*Tendency to crack.*—None observed (dry season).
*Color.*—Black [267. Black] over a Dark purplish red [259. d.pR] background with minor Grayish reddish brown [46. gy.rBr] freckling throughout.
*Bloom.*—Abundant.
Flesh:
*Color.*—Dark red [16. d.R] near skin blending evenly to Pale orange yellow [73. p.OY] toward the stone with Moderate red [15. m.R] veins throughout.
*Surface of pit cavity.*—Covered with Pale orange yellow [73. p.OY] broken fibers when twisted away from stone.
*Amygdalin.*—Moderate.
*Juice.*—Moderate, rich.
*Texture.*—Firm, tough, meaty.
*Fibers.*—Abundant, tough.
*Ripens.*—Slightly earliest toward the apex.
*Flavor.*—A tasty balance of acid and sugar, typically 23 brix.
*Aroma.*—Slight.
*Eating quality.*—Excellent.

STONE

Type: Clingstone.
Form: Oval.
Hilum: Narrow, oblong.
Base: Oblique.
Apex: Acuminate.
Sides: Equal.
Surface: Rough throughout with a groove on each side of the dorsal fin.
External color of stone: Light brown [57. l.Br] when first removed.
Pit wall color when cracked: Light brown [57. l.Br].
Cavity surface color: Strong brown [55. s.Br].
Average pit wall thickness: 1/16" [1.6 mm.]
Average width: ⅝" [15.9 mm.].
Average length: ⅞" [22.2 mm.].
Average breadth: 7/16" [11.1 mm.].
Tendency to split: Slight in a dry season.
Kernel:
*Form.*—Oval.
*Skin Color.*—Strong yellowish brown [74. s.yBr] when first removed.
*Pellicle color.*—Dark grayish yellowish brown [81. d.gy.yBr].
*Vein color.*—Dark yellowish brown [78. d.yBr].
*Taste.*—Bitter.
*Viable.*—Yes.
*Average width.*—13/32" [10.3 mm.].
*Average length.*—9/16" [14.3 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweet V' interspecific tree (U.S. Plant Pat. No. 16,369) by being self-unfruitful and by producing fruit that is clingstone in type, that is mostly globose in shape, that matures in the late season, and that is very good in flavor, but is distinguished therefrom by producing fruit that is mostly black in skin color instead of mostly purple, that has more red and orange in its flesh color, that is larger in size, and that matures about thirty days later.

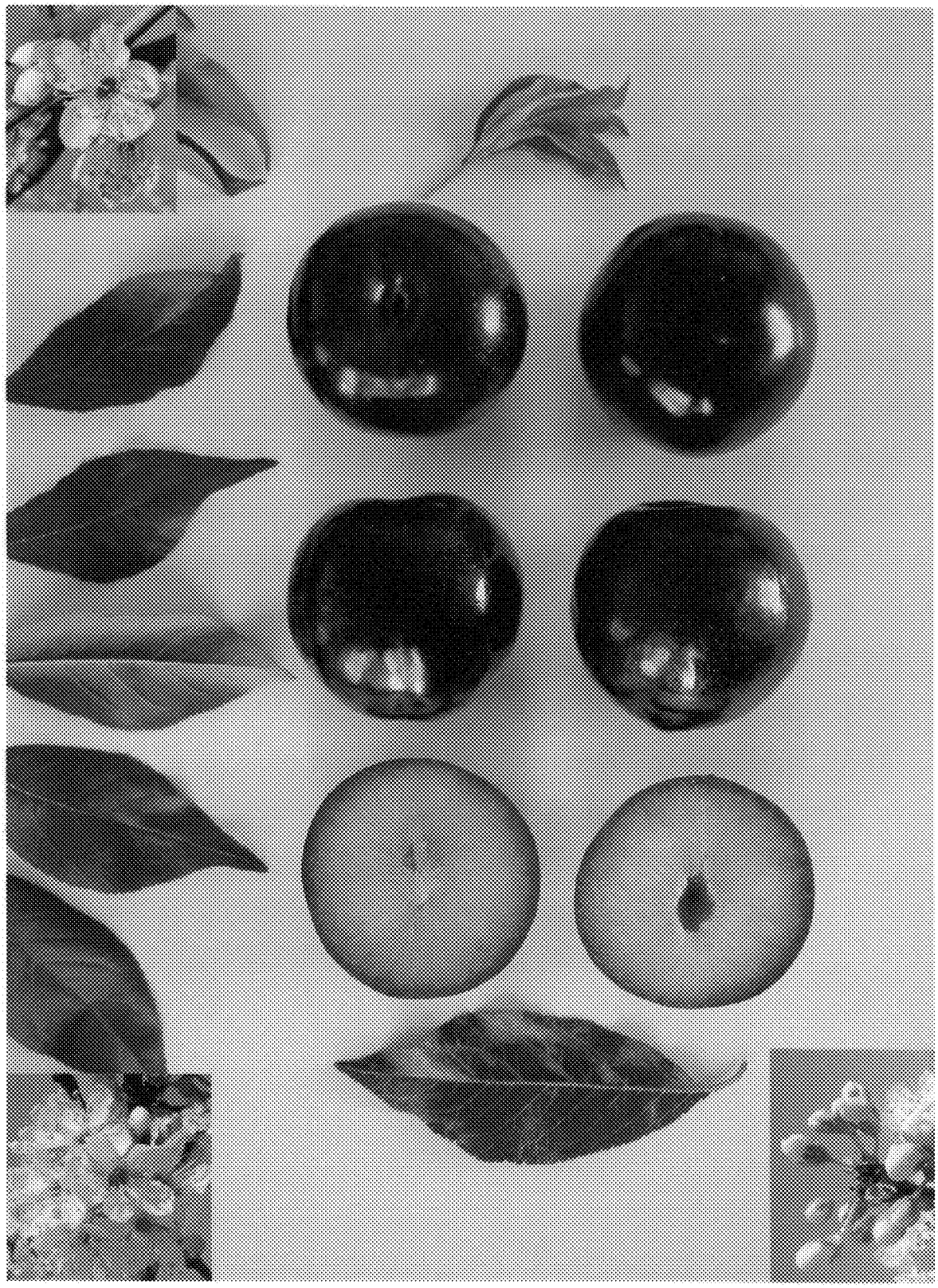

* * * * *